(12) United States Patent
Borges et al.

(10) Patent No.: US 9,108,797 B1
(45) Date of Patent: Aug. 18, 2015

(54) METHODS AND SYSTEMS TO IDENTIFY AND MANAGE RECYCLABLE MATERIALS

(71) Applicant: International Business Machines Corporation, Armonk, NY (US)

(72) Inventors: Gabriel P. Borges, Sumare (BR); Claude Falbriard, Cananeia (BR); Grant D. Miller, Arvada, CO (US); Nader M. Nassar, Yorktown Heights, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 14/481,272

(22) Filed: Sep. 9, 2014

(51) Int. Cl.
*G06K 7/00* (2006.01)
*B65F 1/14* (2006.01)

(52) U.S. Cl.
CPC ......... *B65F 1/1484* (2013.01); *B65F 2210/112* (2013.01)

(58) Field of Classification Search
CPC ............ G06K 19/02; G06K 19/06009; G06K 19/06196; G06K 19/067; G06K 7/00; G06Q 30/0282
USPC .......................................... 235/435, 439, 492
See application file for complete search history.

(56) References Cited

U.S. PATENT DOCUMENTS

| | | | |
|---|---|---|---|
| 8,549,461 B2 | 10/2013 | Huijbregts et al. | |
| 8,550,252 B2* | 10/2013 | Borowski et al. | 209/3 |
| 8,862,495 B2* | 10/2014 | Ritter | 705/14.1 |
| 2006/0080819 A1 | 4/2006 | McAllister | |
| 2008/0094224 A1 | 4/2008 | Parker et al. | |
| 2010/0312601 A1* | 12/2010 | Lin | 705/8 |
| 2011/0279245 A1* | 11/2011 | Hynes et al. | 340/10.42 |
| 2013/0320086 A1* | 12/2013 | Kruglick | 235/435 |

FOREIGN PATENT DOCUMENTS

| | | |
|---|---|---|
| EP | 2038791 | 3/2009 |
| EP | 2188754 | 5/2010 |
| EP | 2195775 | 6/2010 |
| WO | 2012069839 | 5/2012 |

OTHER PUBLICATIONS

Brian Howard Clark, What Do Recycling Symbols on Plastic Mean?, Good Housekeeping, http://www.thedailygreen.com/green-homes/latest/recycling-symbols-plastics-460321, as of Sep. 27, 2012, pp. 1-8.

* cited by examiner

*Primary Examiner* — Seung Lee
(74) *Attorney, Agent, or Firm* — George R. McGuire; John Pivnichny; Bond Schoeneck & King, PLLC

(57) ABSTRACT

A method to identify and manage recyclable materials provides a recyclable material with a quartz crystal identification element configured to oscillate at a predetermined frequency associated with the recyclable material. A mobile device detects the oscillation frequency of the quartz crystal, identifies the recyclable material based on the detected oscillation frequency, and sends that information to a controller. The controller creates handling instructions for the pickup of the identified recyclable material.

20 Claims, 3 Drawing Sheets

METHODS AND SYSTEMS TO IDENTIFY AND MANAGE RECYCLABLE MATERIALS

BACKGROUND

The present invention relates to methods and systems for identifying and managing recyclable materials, and, more particularly, to a method and system for passively detecting recyclable materials and automatically scheduling pickup of those materials.

Recycling is an important aspect of natural resource management and sustainability. Despite this, only a small percentage of resources are adequately recycled or reused every year. In 2009 it is estimated that, for example, a little over 2 million tons of plastics were recycled in the United States. However, since almost 30 million tons of plastics were generated in the United States that same year, only about 6-7% of all plastics generated in 2009 were actually recycled. Similarly, it is estimated that only 25% of all electronics were actually collected for recycling in 2009, with only 8% of mobile phones collected.

Thus, it is clear that not only is there is a continued need for increased awareness of recycling, but also for programs, methods, and systems that facilitate recycling. One of the most complex challenges for recyclers is the identification of the different types of materials that could possibly be recycled, as well as the separation of those different materials when the decision to recycle has been made. The presence of even one wrong item in a recycling batch can sometimes ruin the entire batch. Accordingly, the proper separation of different materials can be essential for efficient and affordable recycling.

In the United States and internationally, for example, plastics are identified by a Society of the Plastics Industry ("SPI") resin identification code. The symbols comprise clockwise arrows that form a rounded triangle enclosing a number from 1 to 7. Each number represents a particular type of plastic, and typically can only be recycled with plastics having the same number. Number 1, as an example, is utilized for the polymer polyethylene terephthalate ("PET" or "PETE"), and is often used for material like plastic soda bottles. Number 3, as another example, is utilized for the polymer polyvinyl chloride ("PVC") and is used as a material for pipes, shower curtains, and children's toys. Items made with PET are commonly recycled by most curbside recycling programs, while items made with PVC are not usually recycled although they are sometimes accepted by plastic lumber makers. The difference between post-consumer handling of items comprising PET and items comprising PVC demonstrates the continued need for the identification, management, and processing of recyclable materials.

BRIEF SUMMARY

Disclosed are methods and systems for managing recyclable materials, including detecting the recyclable materials and automatically scheduling their pickup. Accordingly, embodiments of the disclosure are directed to a method of identifying and managing recyclable materials using a mobile device. According to an embodiment, the materials can be labeled with a thin film of quartz crystals which are designed, programmed, or otherwise enabled to oscillate at a particular predetermined frequency that is associated with the type of material to be recycled. The identifying information can then be used to schedule pickup of the identified material, or to otherwise process or manage the identified material.

Thus, in one aspect, a method to identify and manage recyclable materials includes the steps of: (i) providing a recyclable material with an identification device having a quartz crystal configured to oscillate at a predetermined frequency associated with the recyclable material; (ii) detecting, using a mobile device, the oscillation frequency of the quartz crystal; (iii) identifying the recyclable material based on the detected oscillation frequency; (iv) sending information representative of the identity of the recyclable material to a controller; and (v) creating handling instructions for the pickup of the identified recyclable material.

According to an embodiment, the information representative of the identity of the recyclable material comprises location information about the recyclable material.

According to an embodiment, the handling instructions comprise information about the location of the identified recyclable material, and/or about a vendor authorized to pick up the identified recyclable material, and/or about a time that the identified recyclable material can be picked up.

According to an embodiment, the mobile device comprises a database, the database comprising information about at least one association between an oscillation frequency of a quartz crystal and a recyclable material.

According to an embodiment, the mobile device comprises a GPS receiver.

According to an embodiment, the method includes the step of sending the handling instructions for the pickup of the identified recyclable material to a user.

According to an embodiment, the method includes the step of sending an alert to a user about the handling instructions.

According to an aspect is a system for identifying and managing recyclable materials, the system having: (i) an identification device associated with a recyclable material, the identification device comprising a quartz crystal configured to oscillate at a predetermined frequency associated with the recyclable material; (ii) a mobile device configured to detect the oscillation frequency of the quartz crystal and identify the recyclable material based on the detected oscillation frequency; and (iii) a controller configured to receive from the mobile device information representative of the identity of the recyclable material, and further configured to create handling instructions for the pickup of the identified recyclable material.

According to an embodiment, the information representative of the identity of the recyclable material comprises location information about the recyclable material.

According to an embodiment, the handling instructions comprise information about the location of the identified recyclable material, and/or about a vendor authorized to pick up the identified recyclable material, and/or about a time that the identified recyclable material can be picked up.

According to an embodiment, the mobile device comprises a database, the database comprising information about at least one association between an oscillation frequency of a quartz crystal and a recyclable material.

According to an embodiment, the mobile device comprises a GPS receiver.

According to an embodiment, the controller is further configured to send the handling instructions for the pickup of the identified recyclable material to a user.

According to an embodiment, the controller is further configured to send an alert to a user about the handling instructions.

According to an aspect is a system for identifying and managing recyclable materials, the system having: (i) an identification device associated with a recyclable material, the identification device comprising a quartz crystal configured to oscillate at a predetermined frequency associated with the recyclable material; (ii) a mobile device configured to detect the oscillation frequency of the quartz crystal and identify the recyclable material based on the detected oscillation frequency, the mobile device comprising a database with information about at least one association between an oscillation frequency of a quartz crystal and a recyclable material, and further comprising a GPS receiver; and (iii) a controller configured to receive from the mobile device information representative of the identity and location of the recyclable material, configured to create handling instructions for the pickup of the identified recyclable material, and further configured to send the handling instructions for the pickup of the identified recyclable material to a user.

According to an embodiment, the controller is further configured to send an alert to a user about the handling instructions.

BRIEF DESCRIPTION OF THE SEVERAL VIEWS OF THE DRAWING(S)

The present invention will be more fully understood and appreciated by reading the following Detailed Description in conjunction with the accompanying drawings, in which.

DETAILED DESCRIPTION

While recycling is an essential component of the management and sustainability of natural resources, studies suggest that only a very small percentage of some generated materials—such as plastics—are actually recycled every year. Further, even when these materials are identified for recycling they are sometimes misidentified and/or mishandled which can result in materials of different types being combined in a recycling program, which can damage a recycling program with regard to cost, efficiency, and time.

Accordingly, there is a recognized need for methods and systems that can facilitate the identification, management, and processing of recyclable materials such as plastics, as well as many other types of plastics. For example, an automated system that is used to identify recyclable materials with a sensor and then schedule pickup of that identified material would be beneficial. In recognition of that need, embodiments disclosed herein are directed to methods of identifying and managing recyclable materials using a mobile device. The materials can be labeled with a thin film of quartz crystals which are designed, programmed, or otherwise enabled to oscillate at a particular predetermined frequency that is associated with the type of material to be recycled. The identifying information can then be used to schedule pickup of the identified material, or to otherwise process or manage the identified material.

Figure 1:
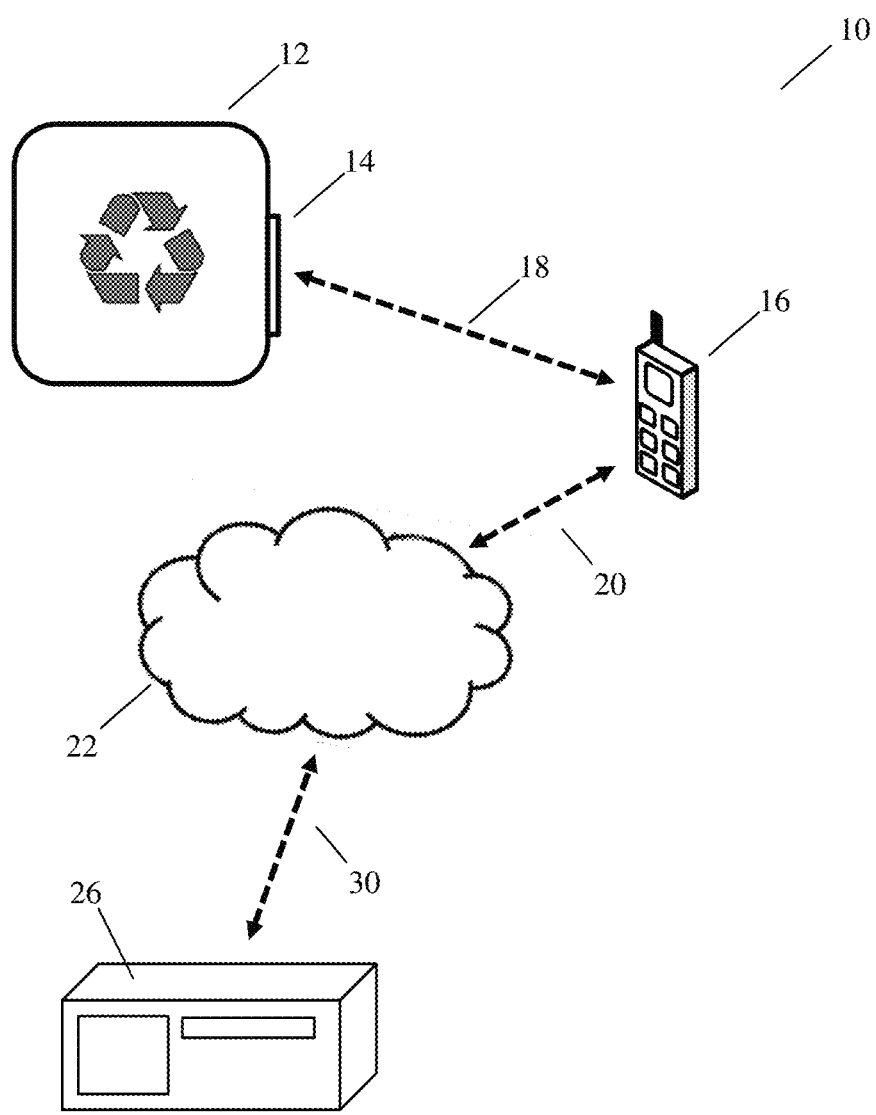
FIG. 1 is a schematic representation of a system for identifying and managing recyclable materials in accordance with an embodiment of the invention.

Referring now to the drawings, wherein like reference numerals refer to like parts throughout, there is seen in FIG. 1 a system 10 for identifying and managing a recyclable material 12. Recyclable material 12 can be any material capable of being recycled, including materials that are not traditionally recycled as part of a curbside pickup program. Some recycling programs are specialized and will only pick up one or two types of materials, while other recycling programs will pick up multiple materials. Some recycling programs or companies will only recycle one material, while other recycling programs or companies will recycle many different types of materials. For example, recyclable material 12 can be, among many other things, paper, plastic, wood, glass, metal, cardboard, compostable, and/or batteries.

In some embodiments, recyclable material 12 contains, comprises, or includes a component that can be passively detected in order to identify the material. For example, recyclable material 12 can include identification component 14. Identification component 14 can be associated with recyclable material 12 in any one or more of a wide variety of methods. According to one embodiment, identification component 14 is all or part of the recyclable packaging that an item was stored in. Alternatively, identification component 14 can be in, on, adhered to, or built into recyclable material 12. For example, identification component 14 can be part of a recyclable wrapper, box, or other packaging. As another example, identification component 14 can be part of the recyclable material 12 itself, such as a portion of an electronic device, a battery, or other recyclable material. Identification component 14 can be associated with recyclable material 12 at the time or point of manufacture, packaging, shipping, retail, and/or disposal, for example. Identification component 14 can be a simple transceiver, or can be associated with a database, processor, or wide variety of other components involved in the embodiments envisioned herein, or other recycling or trash management functions.

According to one embodiment, identification component 14 is a thin layer of quartz or other crystalline material capable of oscillating at a predetermined frequency. A crystal such as quartz can experience the piezoelectric effect, meaning that electric charge accumulates in the crystal in response to applied mechanical stress. Quartz also experiences the opposite effect, called converse piezoelectric effect, where the application of an electrical field creates mechanical deformation in the crystal, and can cause the quartz crystal to oscillate. Thus, for example, applying current to the quartz crystal will induce oscillations. The frequency of oscillation of the quartz crystal is dependent, at least in part, on the thickness of the crystal. The thickness of the crystal, therefore, is one of the many variables that can be designed into the system to allow oscillations at different frequencies.

According to an embodiment, the function of identification component 14 is to identify the item with which the component is associated. For example, an oscillation frequency of the identification component 14, such as a quartz crystal, can be utilized to identify the associated component. Referring to FIG. 1, identification component 14 is associated with recyclable material 12. Identification component 14 is, for example, a quartz crystal having a specific oscillation frequency f, where f is a predetermined value. When a current is applied, the quartz crystal will oscillate at the known frequency f. Since frequency f will be associated in a database with a known recyclable material 12, characterizing frequency f will similarly characterize recyclable material 12 (as well as one or more values of identification component 14).

The current can be applied via a remote component, or can be applied by a component that is already associated with the identification component 14, such as a battery and small circuit that can continuously supply power and cause oscillation, or can supply current in response to a signal, trigger, button, proximity alert, or any of a variety of other inducing mechanisms. According to an embodiment, the use of a remote, reusable component to apply the current to the identification component 14 will increase the recyclability of the material 14 and save on cost of the system.

Thus, according to an embodiment, the quartz crystal is a thin film that oscillates at a certain frequency to identify the recyclable material. Whether the recyclable material is a bottle, can, jar or any type of container such as a small bag, the thin film will oscillate at a certain frequency f when its electrons are "energized" by an energy source. Unlike an RFID tag, however, there is no need for a large number of unique identifiers for materials. Indeed, the number of unique identifiers is small, ranging from as few as 10 or less to 100. Accordingly, the identification component 14 can even be made of a material that is only capable of "broadcasting" a small range of frequencies.

According to an embodiment, a mobile device 16 is utilized to characterize recyclable material 12 using identification component 14. The mobile device can be utilized to send a signal, wave, energy, light, or other triggering mechanism to identification component 14 in order to cause a current to be applied to the oscillating crystal or other identifying agent. The device will then wait to receive information about the oscillating crystal using visual information about mechanical vibrations, using light signals, or using another identifying agent created by and/or emitted by identification component 14. Thus, mobile device 16 can be configured or programmed to actively receive information transmitted by a wireless signal 18 from identification component 14 in response to the triggering agent sent by the mobile device.

Alternatively, mobile device 16 is configured or programmed to passively receive information that is transmitted by a wireless signal 18 from identification component 14. Thus, for example, mobile device 16 can be configured or programmed to await a signal from an identification component 14 at all times, or in response to an activation signal by the user. For example, mobile device 16 can be configured or programmed to search for a signal when the user recognizes a need or possibility for a signal, such as when the user is around recyclable material 12 or in a region, space, room, or area where a recyclable material 12 might be located.

According to yet another embodiment, the mobile device 16 is briefly connected directly to recyclable material 12 and/or identification component 14. The mobile device can supply an activation signal to cause a current to be applied by an associated circuit and battery, or the mobile device can itself supply the current to the oscillator, either directly or via an attachment that is capable of both reaching the mobile device's power supply and transmitting that power to the oscillator.

According to other embodiments, the recyclable material 12 is identified using image recognition, including with a camera such as a smart phone or mobile device camera. Alternatively, the camera can be associated with the identification component 14 or with a storage or management device for the recyclable material 12. The recyclable material 12 could also be identified by manual entry by a user. For example, the user can place plastic of type "2" into a receptacle and then manually enter the type number, location, and/or other information into mobile device 16 or identification component 14. The recyclable material 12 could also be identified by near field communication ("NFC") between identification component 14, the receptacle, mobile device 16, or other components of the system.

Figure 2:
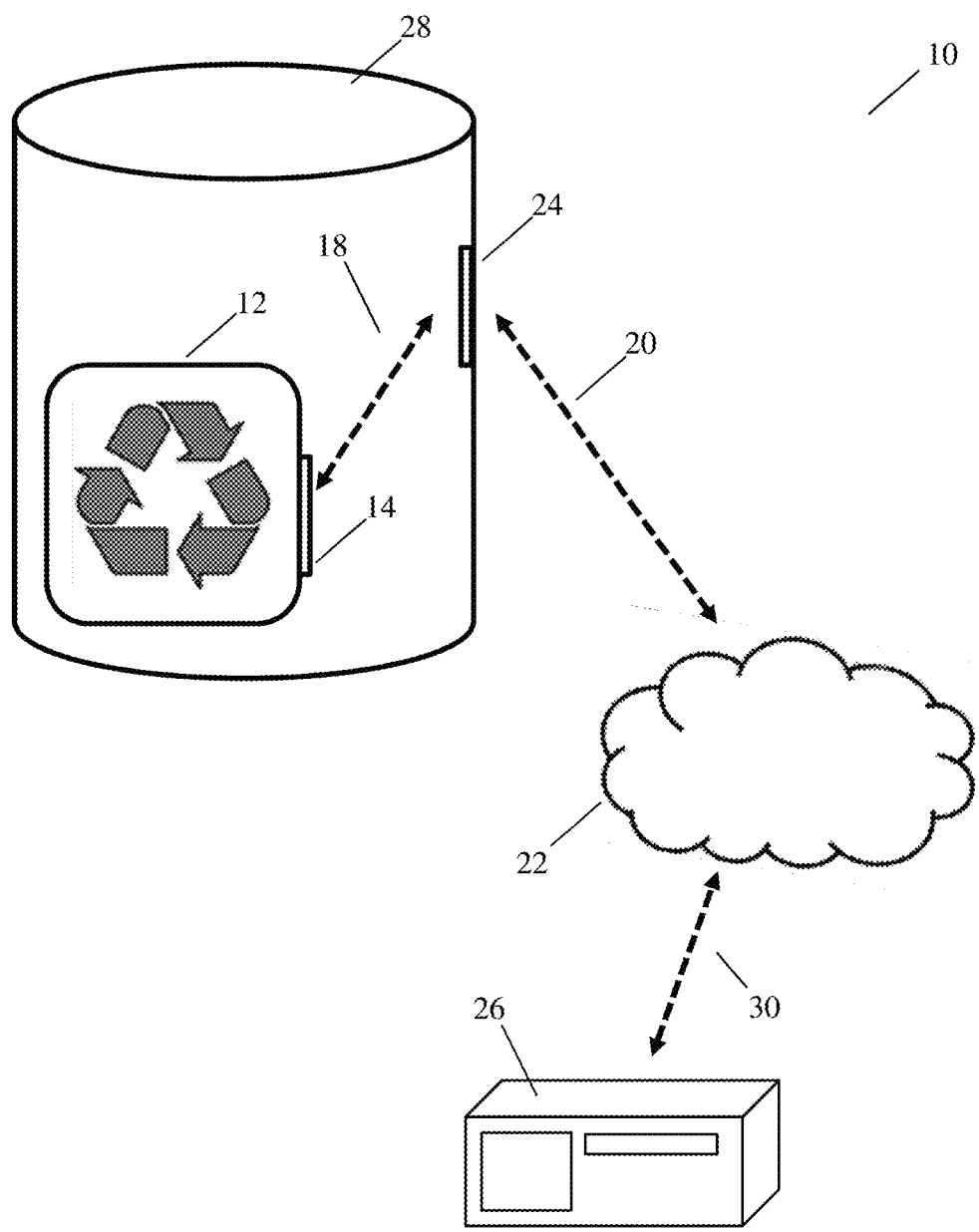
FIG. 2 is a schematic representation of a system for identifying and managing recyclable materials in accordance with an embodiment of the invention.

While FIG. 1 depicts recyclable material 12 with an identification component 14 that communicates directly with a mobile device 16, identification component 14 can also be programmed or configured to communicate with another communication device 24, as shown in FIG. 2. In this example, recyclable material 12 is placed inside receptacle 28. Identification component 14 can send a wired or wireless signal, either passively activated at all times or in response to a trigger, to communication device 24 in order to identify recyclable material 12. For example, communication device 24 can be programmed or designed to send out an activation signal at all times, or in response to the receptacle being opened or moved, or in response to some other detection that recyclable material 12 is in close proximity. For example, the user may cause communication device 24 to communicate with identification component 14 when he or she places the recyclable material 12 inside receptacle 28. Communication device 24 can be a simple transceiver, or can be associated with a database, processor, or wide variety of other components involved in the embodiments envisioned herein, or other recycling or trash management functions, including but not limited to a GPS or other location component.

As an example of a process for identifying recyclable material 12 using the system depicted in FIG. 2, the user initiates the process by placing recyclable material 12 inside receptacle 28. The user initiates identification by pressing a button that activates communication device 24 to send out a signal that causes the quartz crystal to oscillate in response. The oscillation frequency f is detected by communication device 24, and that information is sent to a remote location by wired or wireless signal.

As shown in FIGS. 1 and 2, information about recyclable material 12 can be sent to another location by wired and/or wireless signal in order to cause the material to be picked up for recycling. The information can include only the oscillation information, and/or the location information, and/or identification information about the recyclable material 12 based on the detected oscillation information. In FIG. 1, for example, the information is sent from the mobile device 16 directly or indirectly via wired or wireless transmission 20 and/or 30 to a remote location such as server 26. In FIG. 2 for example, the information is sent from the communication device 24 directly or indirectly via wired or wireless transmission 20 and/or 30 to a remote location such as server 26. These transmissions can include, for example, a network 22 such as the internet or an intranet, among many other options. As an example, mobile device 16 identifies recyclable material 12 based on the oscillation frequency f as plastic with an SPI resin identification code of 1. The mobile device sends a cellular signal to a local cellular tower, which transmits that to and/or via the internet or other network to server 26 which is located at the local recycler's office. Alternatively, the mobile device is connected to a local wifi access point and sends a wifi signal to the transceiver which in turns transmits that via the internet to server 26 located at the recycler's office, or at a location where a recycler can access it remotely or directly.

Rather than store a local database of information that must be regularly or periodically updated, the mobile device 16 and/or the communication device 24 can query a remote database such as server 26, or can simply transmit location and the frequency f and identification information, or just the frequency f information, to the remote location. In the event that the mobile device 16 and/or the communication device 24 are not in the vicinity of a receiver of their signal, they can optionally comprise a database to store location, frequency, and/or identification information that can be batch processed and/or sent when a receiver is available.

According to one embodiment, mobile device 16 can utilize an app, or program application, that is designed to facilitate the identification of recyclable material 12 regardless of the user's relationship to the recyclable material. For example, as the user of mobile device 16 drives to work, the device is set to passively receive any signals from any identification component 14. Together with GPS information, the identification information can be utilized to find the location of the recyclable material 12 by an interested third party. Thus, the GPS information associated with the identity of recyclable material 12 will be sent to a secure, or unsecure, server or database where a third-party can access it. As an example, a recycling entity may want to identify any electronics in the vicinity in order to recapture the electronics for profit or for purely altruistic recycling purposes. The entity will access the database and retrieve information about every electronic device in the vicinity, and can then pursue those electronics based on the associated location information. The system could even be designed as a game, where users and/or recyclers gain points for every item, pound, or other unit of recyclable material 12 that is recycled as a result of their identification and location information. Users and/or recyclers could even earn money as a result of the identification and location information, including but not limited to a share of the profit made from the recycling that occurs.

According to another embodiment, system 10 also manages the pickup of recyclable materials in order to optimize routes and timing and/or to schedule pickup of difficult materials such as waste oil, large batteries, or a wide variety of other hard-to-recycle materials. Indeed, considering the expense of maintaining and powering recycling pickup vehicles, there is a continued need for systems and methods that minimize the use of the recycling pickup vehicle while simultaneously increasing the amount of recyclable materials identified and picked up by the vehicles. As an example, recycling pickup vehicles may normally be sent on a specific day(s) and/or schedule to pick up material. However, there may be no materials available on some days, while on other days there is too much material to pick up.

Accordingly, the system can include a controller, processor, or other scheduling or controlling device to track the location and/or identity of recyclable material 12, and to send out one or more recycling pickup vehicle as needed. The controller, processor, scheduling, or controlling device can be designed or programmed to only schedule a recycling pickup vehicle if a predetermined number of recyclable material is available for pick up, or if a certain threshold of items along a particular route is available for pick up, or if one or more items have been waiting too long (such as a predetermined amount of time) for pick up, or if a certain variety of materials are available for pick up, among many other possible variables including energy, time, and cost savings. According to one embodiment, the controller, processor, scheduling, or controlling device can be designed or programmed to schedule a pickup or alert a user among two or more different recycling companies. For example, company X may only pick up material X, while company Y only picks up material Y. The controller can tell company Y when material Y is available, and tell company X when material X is available.

According to one embodiment of the system, the user, mobile device, or other element identifies the recyclable material 12, the location of recyclable material 12, and/or the amount of recyclable material 12. The system 10 can also look up the type of material to be recycled by sending identification information to a server that compares the received information against a list for updated information. According to an embodiment, special handling instructions can be sent back to the user.

According to another embodiment, system 10 is programmed or configured to send an alert when a pickup is scheduled. For example, system 10 can send a wired and/or wireless signal back through the same communication system that sent the signal from mobile device 16 to the remove server/database/controller 26. Alternatively, system 10 can send a wired and/or wireless signal to another device that a user is monitoring. For example, the alert can be a text message, or a smart phone notification or sound, among many other options. As one example, the notification or alert can be a noise, sound, or message on or in identification component 14, receptacle 28, and/or mobile device 16.

Figure 3:
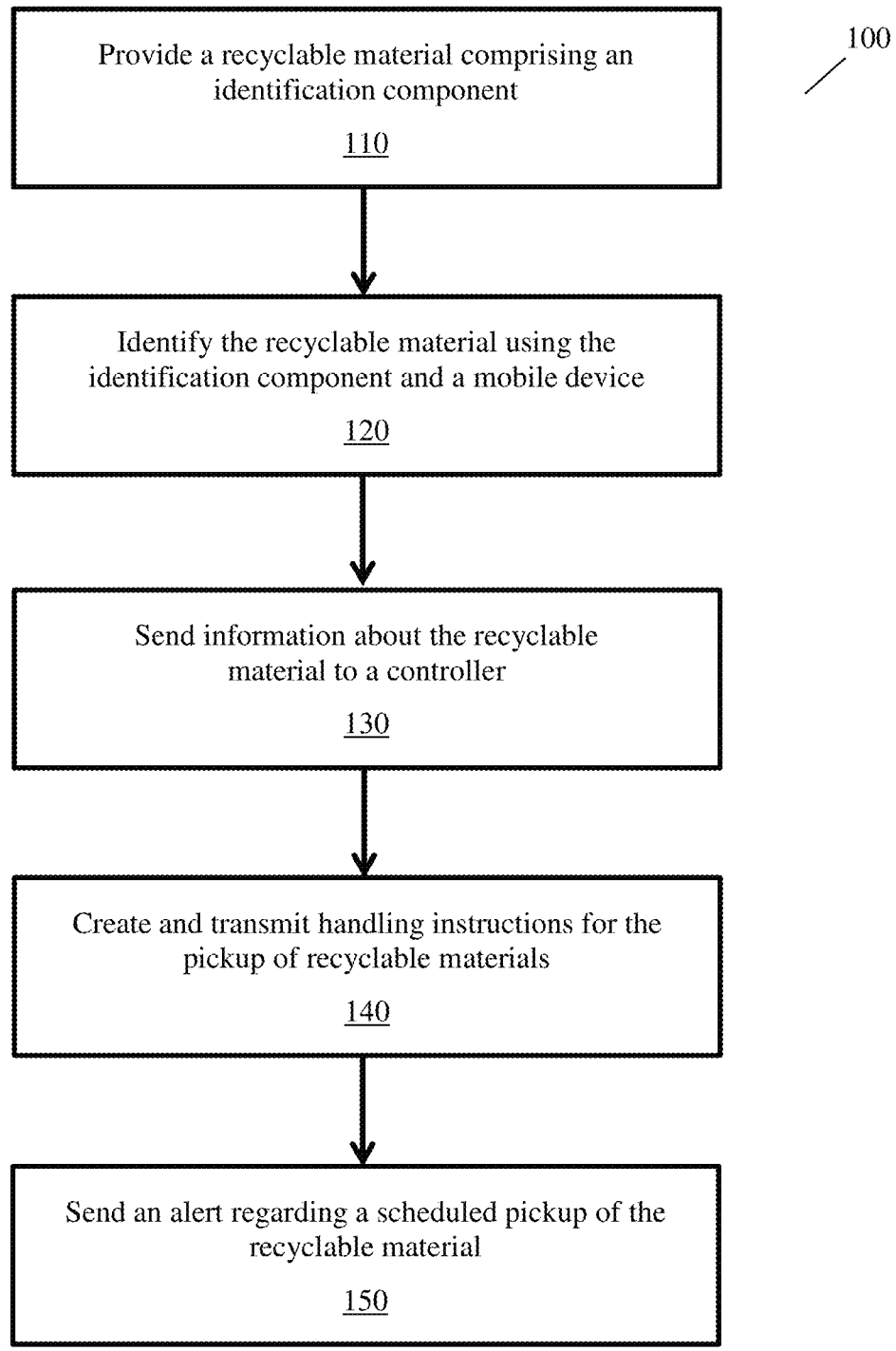
FIG. 3 is a method for identifying and managing recyclable materials in accordance with an embodiment of the invention.

Shown in FIG. 3 is a method 100 for identifying and managing a recyclable material 12. At step 110 of method 100 for identifying and managing a recyclable material, a recyclable material is provided. Recyclable material 12 can be any material capable of being recycled, including materials that are not traditionally recycled as part of a curbside pickup program. For example, recyclable material 12 can be, among many other things, paper, plastic, wood, glass, metal, cardboard, compostable, and/or batteries. Recyclable material 12 contains, comprises, or includes a component that can be passively detected in order to identify the material. For example, recyclable material 12 can include identification component 14. Identification component 14 can be associated with recyclable material 12 in any one or more of a wide variety of methods. According to one embodiment, identification component 14 is all or part of the recyclable packaging that an item was stored in. Alternatively, identification component 14 can be in, on, adhered to, or built into recyclable material 12. For example, identification component 14 can be part of a recyclable wrapper, box, or other packaging. As another example, identification component 14 can be part of the recyclable material 12 itself, such as a portion of an electronic device, a battery, or other recyclable material. Identification component 14 can be associated with recyclable material 12 at the time or point of manufacture, packaging, shipping, retail, and/or disposal, for example. Identification component 14 can be a simple transceiver, or can be associated with a database, processor, or wide variety of other components involved in the embodiments envisioned herein, or other recycling or trash management functions. According to one embodiment, identification component 14 is a thin layer of quartz or other crystalline material capable of oscillating at a predetermined frequency.

At step 120 of method 100, the system identifies the recyclable material 12. For example, according to an embodiment the function of identification component 14 is to identify the item with which the component is associated. For example, an oscillation frequency of the identification component 14, such as a quartz crystal, can be utilized to identify the associated component. Identification component 14 is, for example, a quartz crystal having a specific oscillation frequency f, where f is a predetermined value. When a current is applied, the quartz crystal will oscillate at the known frequency f. Since frequency f will be associated in a database with a known recyclable material 12, characterizing frequency f will similarly characterize recyclable material 12 (as well as one or more values of identification component 14). According to an embodiment, mobile device 16 is utilized to characterize recyclable material 12 using identification component 14. The mobile device can be utilized to send a signal, wave, energy, light, or other triggering mechanism to identification component 14 in order to cause a current to be applied to the oscillating crystal or other identifying agent. The device will then wait to receive information about the oscillating crystal using visual information about mechanical vibrations, using light signals, or using another identifying agent created by and/or emitted by identification component 14. Thus, mobile device 16 can be configured or programmed to actively receive information transmitted by a wireless signal 18 from identification component 14 in response to the triggering agent sent by the mobile device. Alternatively, mobile device 16 is configured or programmed to passively receive information that is transmitted by a wireless signal 18 from identification component 14. According to other embodiments, the recyclable material 12 is identified using image recognition, manual entry by a user, and/or near field communication ("NFC") between identification component 14, the receptacle, mobile device 16, or other components of the system. Identification component 14 can also be programmed or configured to communicate with another communication device 24, as shown in FIG. 2. In this example, recyclable material 12 is placed inside receptacle 28. Identification component 14 can send a wired or wireless signal, either passively activated at all times or in response to a trigger, to communication device 24 in order to identify recyclable material 12. For example, communication device 24 can be programmed or designed to send out an activation signal at all times, or in response to the receptacle being opened or moved, or in response to some other detection that recyclable material 12 is in close proximity. Communication device 24 can be a simple transceiver, or can be associated with a database, processor, or wide variety of other components involved in the embodiments envisioned herein, or other recycling or trash management functions, including but not limited to a GPS or other location component.

At step 130 of method 100, information about the recyclable material 12 is sent to a controller by wired and/or wireless signal in order to cause the material to be picked up for recycling. The information can include only the oscillation information, and/or the location information, and/or identification information about the recyclable material 12 based on the detected oscillation information. In FIG. 1, for example, the information is sent from the mobile device 16 directly or indirectly via wired or wireless transmission 20 and/or 30 to a remote location such as server 26. In FIG. 2 for example, the information is sent from the communication device 24 directly or indirectly via wired or wireless transmission 20 and/or 30 to a remote location such as server 26. These transmissions can include, for example, a network 22 such as the internet or an intranet, among many other options. As an example, mobile device 16 identifies recyclable material 12 based on the oscillation frequency f as plastic with an SPI resin identification code of 1. The mobile device sends a cellular signal to a local cellular tower, which transmits that to and/or via the internet or other network to server 26 which is located at the local recycler's office. Alternatively, the mobile device is connected to a local wifi access point and sends a wifi signal to the transceiver which in turns transmits that via the internet to server 26 located at the recycler's office, or at a location where a recycler can access it remotely or directly.

At step 140 of method 100, the system creates and transmits handling instructions for the pickup of recyclable materials. The handling instructions can include, for example, a time that the items will be picked up, where the controller identifies a vendor list based on location for handling the identified materials and routes a pickup request to an appropriate company, simultaneously optimizing a pickup time, route, and/or other factors. According to an embodiment, the controller, processor, scheduling, or controlling device can be designed or programmed to only schedule a recycling pickup vehicle if a predetermined number of recyclable material is available for pick up, or if a certain threshold of items along a particular route is available for pick up, or if one or more items have been waiting too long (such as a predetermined amount of time) for pick up, or if a certain variety of materials are available for pick up, among many other possible variables including energy, time, and cost savings. According to one embodiment, the controller, processor, scheduling, or controlling device can be designed or programmed to schedule a pickup or alert a user among two or more different recycling companies.

At step 150 of method 100, the system optionally sends out an alert when a pickup is scheduled. As a result, one or more elements of system 10 is programmed or configured to send an alert. For example, system 10 can send a wired and/or wireless signal back through the same communication system that sent the signal from mobile device 16 to the remove server/database/controller 26. Alternatively, system 10 can send a wired and/or wireless signal to another device that a user is monitoring. For example, the alert can be a text message, or a smart phone notification or sound, among many other options.

While various embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings is/are used. Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, embodiments may be practiced otherwise than as specifically described and claimed. Embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

A "module" or "component" as may be used herein, can include, among other things, the identification of specific functionality represented by specific computer software code of a software program. A software program may contain code representing one or more modules, and the code representing a particular module can be represented by consecutive or non-consecutive lines of code.

As will be appreciated by one skilled in the art, aspects of the present invention may be embodied/implemented as a computer system, method or computer program product. The computer program product can have a computer processor or neural network, for example, that carries out the instructions of a computer program. Accordingly, aspects of the present invention may take the form of an entirely hardware embodiment, an entirely software embodiment, and entirely firmware embodiment, or an embodiment combining software/firmware and hardware aspects that may all generally be referred to herein as a "circuit," "module," "system," or an "engine." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction performance system, apparatus, or device.

The program code may perform entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

The flowcharts/block diagrams in the Figures illustrate the architecture, functionality, and operation of possible implementations of systems, methods, and computer program products according to various embodiments of the present invention. In this regard, each block in the flowcharts/block diagrams may represent a module, segment, or portion of code, which comprises instructions for implementing the specified logical function(s). It should also be noted that, in some alternative implementations, the functions noted in the block may occur out of the order noted in the figures. For example, two blocks shown in succession may, in fact, be performed substantially concurrently, or the blocks may sometimes be performed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

What is claimed is:

1. A computer implemented method to identify and manage recyclable materials, the method comprising the steps of:
   providing a recyclable material, wherein the recyclable material comprises an identification device, the identification device comprising a quartz crystal configured to oscillate at a predetermined frequency associated with the recyclable material;
   detecting, using a mobile device, the oscillation frequency of the quartz crystal;
   identifying the recyclable material based on the detected oscillation frequency;
   sending information representative of the identity of the recyclable material to a controller;
   creating handling instructions for the pickup of the identified recyclable material.

2. The method of claim 1, wherein the information representative of the identity of the recyclable material comprises location information about the recyclable material.

3. The method of claim 1, wherein the handling instructions comprise information about the location of the identified recyclable material.

4. The method of claim 1, wherein the handling instructions comprise information about a vendor authorized to pick up the identified recyclable material.

5. The method of claim 1, wherein the handling instructions comprise information about a time that the identified recyclable material can be picked up.

6. The method of claim 1, wherein the mobile device comprises a database, the database comprising information about at least one association between an oscillation frequency of a quartz crystal and a recyclable material.

7. The method of claim 1, wherein the mobile device comprises a GPS receiver.

8. The method of claim 1, further comprising the step of sending the handling instructions for the pickup of the identified recyclable material to a user.

9. The method of claim 1, further comprising the step of sending an alert to a user about the handling instructions.

10. A system for identifying and managing recyclable materials, the system comprising:
    an identification device associated with a recyclable material, the identification device comprising a quartz crystal configured to oscillate at a predetermined frequency associated with the recyclable material;
    a mobile device configured to detect the oscillation frequency of the quartz crystal and identify the recyclable material based on the detected oscillation frequency; and
    a controller configured to receive from the mobile device information representative of the identity of the recyclable material, and further configured to create handling instructions for the pickup of the identified recyclable material.

11. The system of claim 10, wherein the information representative of the identity of the recyclable material comprises location information about the recyclable material.

12. The system of claim 10, wherein the handling instructions comprise information about the location of the identified recyclable material.

13. The system of claim 10, wherein the handling instructions comprise information about a vendor authorized to pick up the identified recyclable material.

14. The system of claim 10, wherein the handling instructions comprise information about a time that the identified recyclable material can be picked up.

15. The system of claim 10, wherein the mobile device comprises a database, the database comprising information about at least one association between an oscillation frequency of a quartz crystal and a recyclable material.

16. The system of claim 10, wherein the mobile device comprises a GPS receiver.

17. The system of claim 10, wherein the controller is further configured to send the handling instructions for the pickup of the identified recyclable material to a user.

18. The system of claim 10, wherein the controller is further configured to send an alert to a user about the handling instructions.

19. A system for identifying and managing recyclable materials, the system comprising:
    an identification device associated with a recyclable material, the identification device comprising a quartz crystal configured to oscillate at a predetermined frequency associated with the recyclable material;
    a mobile device configured to detect the oscillation frequency of the quartz crystal and identify the recyclable material based on the detected oscillation frequency, the mobile device comprising a database with information about at least one association between an oscillation frequency of a quartz crystal and a recyclable material, and further comprising a GPS receiver; and a controller configured to receive from the mobile device information representative of the identity and location of the recyclable material, configured to create handling instructions for the pickup of the identified recyclable material, and further configured to send the handling instructions for the pickup of the identified recyclable material to a user.

20. The system of claim 19, wherein the controller is further configured to send an alert to a user about the handling instructions.

* * * * *